United States Patent [19]
Eckhoff

[11] Patent Number: 5,728,162
[45] Date of Patent: Mar. 17, 1998

[54] ASYMMETRIC CONDYLAR AND TROCHLEAR FEMORAL KNEE COMPONENT

[75] Inventor: Donald G. Eckhoff, Denver, Colo.

[73] Assignee: Board of Regents of University of Colorado, Boulder, Colo.

[21] Appl. No.: 334,385

[22] Filed: Nov. 3, 1994

Related U.S. Application Data

[63] Continuation of Ser. No. 11,489, Jan. 28, 1993, abandoned.

[51] Int. Cl.⁶ ............................................. A61F 2/38
[52] U.S. Cl. ............................................. 623/20
[58] Field of Search .................... 623/18, 20, 16

[56] References Cited

U.S. PATENT DOCUMENTS

| | | | |
|---|---|---|---|
| 3,748,662 | 7/1973 | Helfet | 623/20 |
| 3,798,679 | 3/1974 | Ewald | 623/20 |
| 4,178,641 | 12/1979 | Grindei et al. | 623/20 |
| 4,462,120 | 7/1984 | Ranbert et al. | 623/20 |
| 4,470,158 | 9/1984 | Pappas et al. | 623/20 |
| 4,714,472 | 12/1987 | Averill et al. | 623/20 |
| 4,770,663 | 9/1988 | Hanslik et al. | 623/20 |
| 4,944,756 | 7/1990 | Kenna | 623/20 |
| 5,133,759 | 7/1992 | Turner | 623/20 |

*Primary Examiner*—David Isabella
*Attorney, Agent, or Firm*—Greenlee, Winner and Sullivan, P.C.

[57] ABSTRACT

A surgical method for reducing post-operative knee failure in a knee undergoing arthroplasty by determining the pre-operative lateral displacement of the trochlear groove with respect to the femoral condyles, inserting a prosthetic implant with the condylar members having a lateral displacement which is a function of the determined pre-operative lateral displacement of the sulcus. The invention further includes an device which includes condyle members that are joined by an arched region, said region have a lateral displacement of between 1 mm and 15 mm with respect to said condyle members. The subject device addresses the problems of implant failure due to compressive force on the patella.

6 Claims, 2 Drawing Sheets

ASYMMETRIC CONDYLAR AND TROCHLEAR FEMORAL KNEE COMPONENT

This application is a continuation of application Ser. No. 08/011,489 Jan. 28, 1993, now abandoned.

BACKGROUND OF THE INVENTION

1. Field of the Invention

The present invention relates to a method and apparatus for reducing post-operative failure of a knee in a patient undergoing total knee arthroplasty.

2. Description of the Prior Art

The replacement of the knee has become a common surgical procedure when the natural knee components have either worn out from repeated stress or from advanced disease. A frequent and serious problem in total knee arthroplasty is failure of the implant. This failure is often a result of compression, stress, and improper fit of the implant which may not closely approximate the patient's natural knee.

It has been noted by leading surgeons in the field that the shape of the condyles, relative to the trochlea of the prosthesis to be implanted, is one of the most important factors influencing post-operative knee function. Therefore, the shape of such an implant is directly related to the implanted prosthesis survival.

As a commercial consideration, devices are mass-manufactured in order to maximize efficiency in manufacturing the prosthesis. Because of the manner in which the devices are mass-manufactured, it is difficult to take into account the overall individual nature of the knee size of a patient. Accordingly, the present devices used for the total replacement of the anatomical knee joint, in particular the design of the femoral component, have generally tended to be symmetrical in design.

Present technology does not sufficiently reflect the variations of physical characteristics of individuals. Therefore, use of standardized types of prostheses in total knee arthroplasty, without taking into consideration the anatomy of the patient, can result in excessive compression force on the patellar component at the patella's lateral femoral condyle articulation, producing patellar component failure with unacceptable frequency. These failures result in decreased range of motion due to tightness of the patella as it moves over the condyle during flexion and extension of the knee, with the need for eventual replacement of the implant. Vertical asymmetrical condyles, as shown in U.S. Pat. No. 5,133,759 issued to Turner, have been proposed to address the lack of fit problem, but provide only a partial solution to the problem of patella displacement.

Accordingly, it is an object of the present invention to improve apparatus and techniques for knee replacement prosthesis to more clearly approximate the normal anatomy of the knee. It is a further object of the present invention to reduce the compressive force on the patellar component so as to reduce the failure rate of an artificial knee.

The present invention reduces post-operative failure of the patella and overcomes the inadequate fit problem associated with the present devices. In accordance with the technique of this invention, there is provided a method for reducing post-operative knee failure in a patient undergoing arthroplasty.

Examples of prior art devices of this general nature can be found in U.S. Pat. Nos. 4,769,040, 4,888,020, 4,950,298, and 4,963,152. A related prior art device can be found in U.S. Pat. No. 5,133,759.

SUMMARY OF THE INVENTION

The present invention enables the replacement of a prosthetic knee with asymmetric condylar and trochlear femoral components which more closely approximates the motion of the natural knee, thereby reducing the risk of implant failure. It is generally recognized that due to the geometrical characteristics of both the medial and lateral condyles and trochlear groove in knee arthroplasty surgery, some patients will experience post-operative failure due to the compressive forces on the patella. The present invention includes both a device and surgical method for overcoming such a result.

The present invention includes a device for knee replacement, said device having a lateral femoral condyle member and a medial femoral condyle member, said condyle members being joined by an arched region, wherein the arched region is provided with a lateral displacement of between 1 mm and 15 mm, most preferably between 3 mm and 8 mm.

It is further anticipated that the prosthetic device for total knee replacement will include a lateral femoral condyle member and a medial femoral condyle member, said members being joined by an arched region, wherein the medial femoral condyle member is provided with a width greater than said lateral femoral condyle.

It is further anticipated that the device will be made out of bio-compatible implantable-grade material, for example, chrome alloy, titanium, or ceramic.

The surgical method of the present invention comprises the determination of pre-operative lateral displacement of the trochlear groove with respect to the femoral condyles. The preferred method of determining the degree of displacement uses known technology, for example, a CT scan measurement. The implant is then inserted, said implant comprising a medial femoral condyle and a lateral femoral condyle, which condyle members have a lateral displacement which has been previously determined by the preoperative lateral displacement of the sulcus. Additionally, the invention includes a method for determining the lateral displacement of the sulcus with respect to the midpoint of the base line. In a preferred embodiment, the medial condyle member has a width greater than the lateral femoral condyle member, so as to lateralize the trochlea and its low point, i.e. sulcus. In a further embodiment the condyle members are vertically asymmetrically positioned relative to each other.

It is well-recognized that surgeons must provide for more complete compatibility and stability during surgery, the post-operative period, and the life of the successful implant of a total knee arthroplasty. The present invention provides both a method and device which accounts for the lateral displacement of the sulcus with respect to the condyles, thereby resulting in a prosthesis that more closely resembles a natural knee. In accordance with an embodiment of the invention, there is provided a means for determining the lateral displacement of the sulcus with respect to the condyles. In accordance with a further feature of the invention, condyles having different widths are employed.

BRIEF DESCRIPTION OF THE DRAWINGS

The present invention will now be described, by way of example, with reference to the accompanying drawings in which.

DETAILED DESCRIPTION

Figure 1:
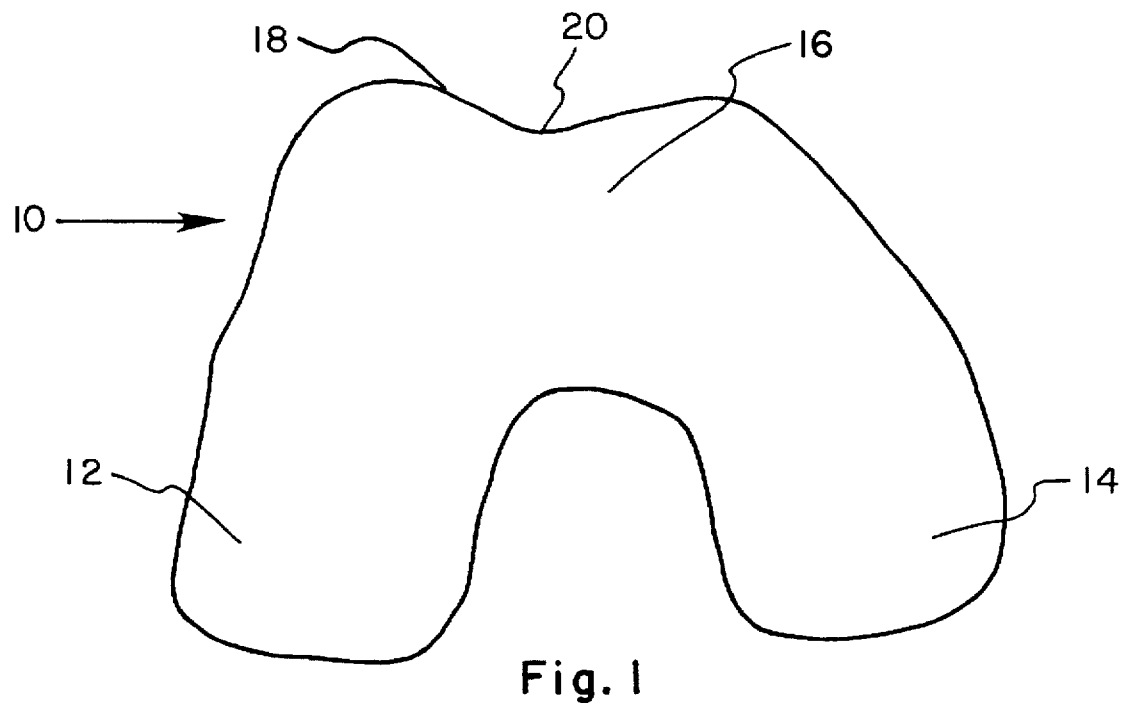
FIG. 1 is a frontal view of a distal femur of the present invention.

The present invention, shown generally at 10, comprises a lateral femoral condyle member 12, a medial femoral condyle member 14, said condyle members being joined by an arched region 16. The arched region 16 is provided with a lateral displacement of, from about 1 mm to 15 mm, most preferably from about 3 mm to 8 mm. The lateral femoral condyle member 12 is vertically asymmetrically positioned relative to the medial condyle member 14. The device further includes a lateral femoral condyle member 12, and a medial femoral condyle member 14 being joined by an arched region 16, wherein the medial femoral condyle 14 has a width greater than said lateral femoral condyle 12.

Additionally, the present invention includes a method wherein the lateral displacement of the trochlear groove 18, is first determined with respect to the femoral condyle 12. The device 10, comprising a medial condyle member 14, and a lateral condyle member 12, having a lateral displacement of, from about 1 mm to 15 mms, most preferably 3 mm to 8 mm, is then inserted.

In a preferred embodiment, the method of determining the lateral displacement of the trochlear groove 18 is most preferably by the CT Scan image System. In this procedure, a CT scan is taken of the patient's distal femur. The CT Scan X-Ray image is then magnified, preferably from about 1× power to 5× power, most preferably from about 2× power to 3× power.

The second step of the method of the present invention is to determine the lateral displacement of trochlear groove 18, by locating the lowest point on the lateral and medial condyle members 12, and 14 respectively.

Additional analytical instruments which will provide the necessary measurements to determine the lateral displacement of the trochlear groove 18 are transparent overlays which may be superimposed on the CT Scan.

Referring, now more particularly to FIG. 1, the device generally shown at 10 includes femoral condyle member 12, medial condyle member 14, arched region 16 between the condyles, trochlear groove 18, and sulcus 20.

Figure 2:
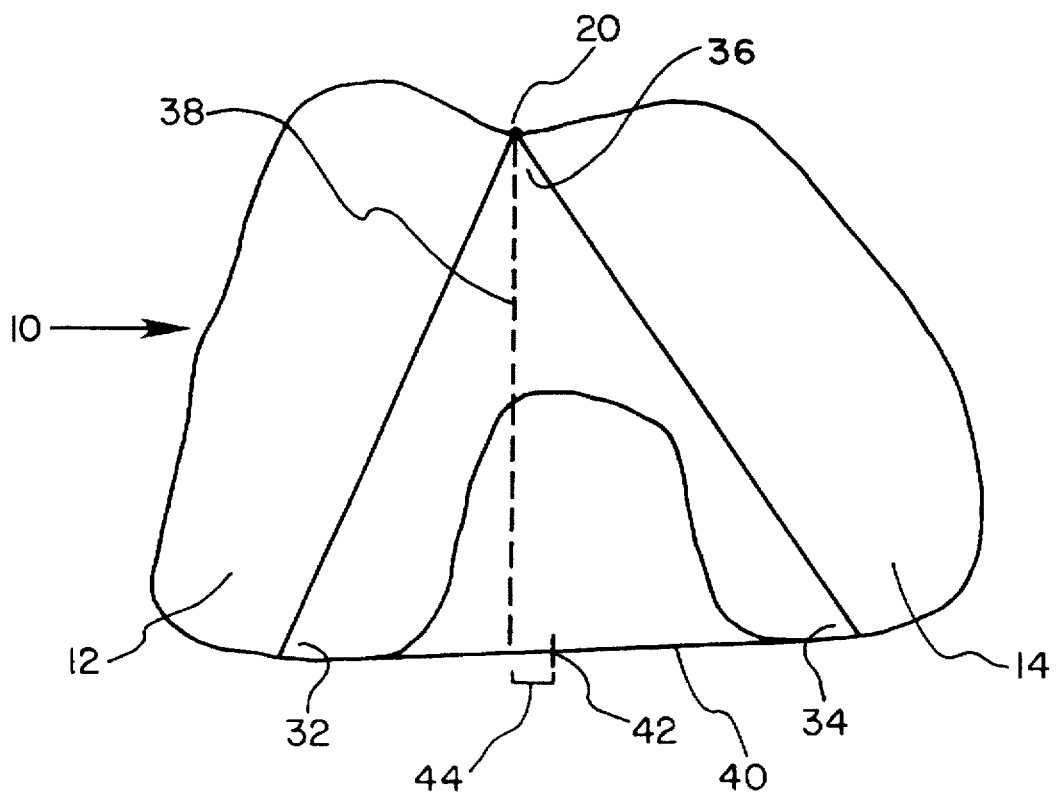
FIG. 2 is a detailed view of distal femur of the present invention.

In FIG. 2, the device is shown with the lateral base angle 32, medial base angle 34, and the apex angle 36. In determining the critical positioning of the prosthetic sulcus 20, a line is drawn extending from femoral condyle member 12 to the sulcus 20, and from medial condyle member 14 to sulcus 20. A second line is provided, connecting the femoral condyle member 12 and the medial condyle member 14, said line is determined to be the base line 40. A triangle is then formed by joining these points, creating the lateral base angle 32, medial base angle 34. Once the angles are determined, the resulting apex angle 36 is located.

In determining the lateral displacement of the trochlear groove 18, a perpendicular line 38 is proposed from the sulcus 20 to the base line 40. The base line 40 is then bisected 42 and the lateral displacement 44 is the distance between the perpendicular and the mid-point 42 on the base line 40.

Figure 3:
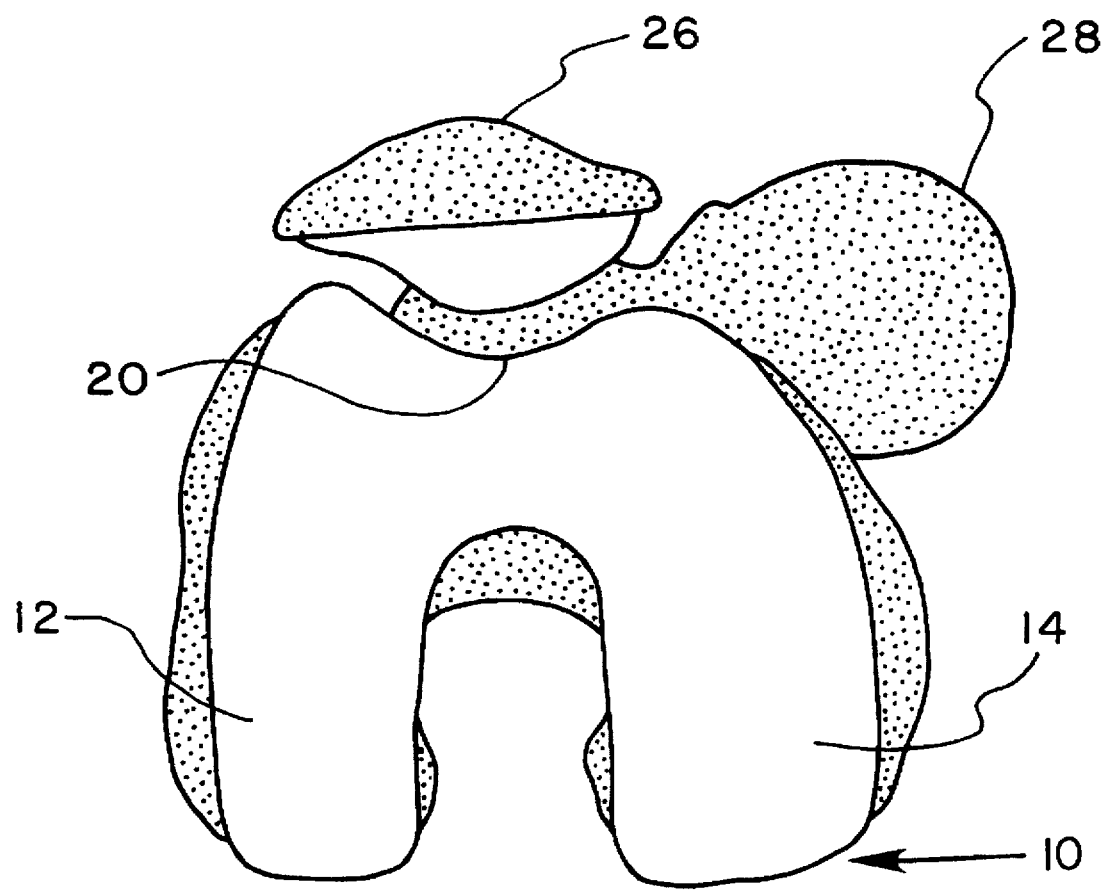
FIG. 3 is prosthetic device implanted on the femur.

Referring now more particularly to FIG. 3, the present invention 10 is shown implanted on the distal femur 28 and articulating with the patella 26. The lateral location of the sulcus 20 has been re-created in the prosthetic device. Also, the respective widths of condylar members 12 and 14 have been accounted for in the implanted device. Since the individual's anatomic structure has been accounted for in terms of lateral displacement and condylar width, the use of this prosthesis permits the patella 26 to more nearly mimic the normal movement in its travel as the knee is bent or extended.

In use, as an illustrated embodiment hereof, a base line is drawn between the two points on the bottom of the condylar members, 12 and 14 respectively, and a triangle is formed by providing a third point at the sulcus 20. In order to determine the lateral displacement of the trochlear groove 18, the bottom leg of the triangle between the lateral base angle 32 and the medial base angle 34 is bisected to obtain a mid-point; a perpendicular line 38 is drawn from the sulcus 20 to the base line 40. The distance on the base line 40 between the mid-point 42 and the perpendicular line 38 is used as a measure of the lateral displacement 44. The lateral displacement 44 of the trochlear groove 18 of the device 10 can then be matched in the prosthetic device used in the operation.

The manufactured prosthetic devices, particularly the component parts, can be made from, for example, cobalt-chrome alloy, titanium, or ceramic.

Further, the preferred lateral displacement in the prosthetic device is between 3 mm and 8 mm. Most preferably, the lateral displacement is 5 mm. The width of the medial femoral condyle can be manufactured to be between 3 mm and 8 mm wider than the lateral femoral condyle, with a preferred difference in width of 5 mm.

The present invention may be subject to many modifications and changes which would be apparent to one skilled in the art. The present embodiment is therefore to be considered in all respects as being illustrative and not restrictive of the scope of the invention as defined by the appended claims. While the invention has been described in its preferred embodiment, it is to be appreciated that variations may be made without departing from the true scope and spirit of the invention.

What is claimed is:

1. A prosthetic device for knee replacement comprising:

a lateral femoral condyle member having a curved lateral surface, having a lowermost point, and having a top;

a medial femoral condyle member having a lowermost point and having a top; said medial femoral condyle member being joined to said lateral femoral condyle member forming a junction between the tops of the two condycles such that an arched region having a top is formed between said members;

a trochlear groove at the top of said prosthetic device at the junction between said lateral femoral and medial femoral condyle members;

a sulcus, being the lowermost point in said trochlear groove;

wherein the intersection, of a line from said sulcus perpendicular to a baseline joining the lowermost points of said condyle members, with said baseline, is laterally displaced from a point at which the baseline is bisected, said lateral displacement being from about 1 mm to about 15 mm, and wherein said medial femoral condyle member has a width greater than said lateral femoral condyle member.

2. The prosthetic device of claim 1 wherein said lateral displacement is from about 3 mm to about 8 mm.

3. The prosthetic device of claim 1 wherein said lateral and medial femoral condyle members' are vertically displaced in respect to each other.

4. The prosthetic device of claim 1 made of biocompatible material.

5. A knee replacement method comprising the steps of:
   (a) determining the preoperative position of the sulcus of the distal femur to be replaced with respect to the medial and lateral femoral condyles thereof by producing an image of said distal femur to be replaced and determining on said image the lateral displacement of the intersection, of a line from said sulcus perpendicular to a baseline joining the lowermost points of said condyles, with said baseline, from a point at which the baseline is bisected;
   (b) preparing a prosthetic device having the same lateral displacement, said lateral displacement being from about 1 mm to about 15 mm;
   (c) replacing the distal femur with said prosthetic device.

6. The method of claim 5 wherein said lateral displacement is between about 3 mm and about 8 mm.

* * * * *